(12) United States Patent
Isaac et al.

(10) Patent No.: US 9,382,116 B2
(45) Date of Patent: Jul. 5, 2016

(54) MIXTURES FOR PRODUCING CHLORINE DIOXIDE GAS IN ENCLOSURES AND METHODS OF MAKING THE SAME

(71) Applicant: ICA TriNova, LLC, Newnan, GA (US)

(72) Inventors: Thomas L. Isaac, Newnan, GA (US); Joel D. Tenney, Marietta, GA (US)

(73) Assignee: ICA Trinova, LLC, Newnan, GA (US)

( * ) Notice: Subject to any disclaimer, the term of this patent is extended or adjusted under 35 U.S.C. 154(b) by 0 days.

(21) Appl. No.: 14/152,595

(22) Filed: Jan. 10, 2014

(65) Prior Publication Data

US 2014/0193522 A1    Jul. 10, 2014

Related U.S. Application Data

(60) Provisional application No. 61/750,965, filed on Jan. 10, 2013.

(51) Int. Cl.
    *C01B 7/00*      (2006.01)
    *C01B 11/02*     (2006.01)
    *A01N 59/00*     (2006.01)

(52) U.S. Cl.
    CPC .............. *C01B 11/024* (2013.01); *A01N 59/00* (2013.01); *C01B 11/022* (2013.01); *C01B 11/023* (2013.01)

(58) Field of Classification Search
    USPC .......................................... 423/477, 462, 478
    See application file for complete search history.

(56) References Cited

U.S. PATENT DOCUMENTS

| | | | |
|---|---|---|---|
| 2,163,793 A | 6/1939 | Logan | |
| 2,482,891 A | 9/1949 | Ashton | |
| 2,885,368 A | 5/1959 | Hess et al. | |
| 3,049,399 A | 8/1962 | Gamson et al. | |
| 3,271,242 A | 9/1966 | McNicholas | |
| 3,298,780 A | 1/1967 | Fleck | |
| 3,382,033 A | 5/1968 | Kitagawa | |
| 3,997,462 A | 12/1976 | Denaeyer | |
| 4,247,531 A | 1/1981 | Hicks | |
| 4,528,171 A | 7/1985 | Casci et al. | |
| 4,547,381 A | 10/1985 | Mason et al. | |

(Continued)

FOREIGN PATENT DOCUMENTS

| | | |
|---|---|---|
| EP | 0132049 | 1/1985 |
| JP | 52038028 | 3/1977 |

(Continued)

OTHER PUBLICATIONS

Bowman et al., Treatment of Waters Contaminated with BTX and Heavy Metals Using Tailored Zeolites, New Mexico Waste-Management and Education Research Consortium, Technical Completion Report (Project No. WERC-91-41), Mar. 1993, pp. 119-144, U S A.

(Continued)

*Primary Examiner* — James McDonough

(74) *Attorney, Agent, or Firm* — Meunier Carlin & Curfman LLC

(57) ABSTRACT

The present disclosure relates to a mixture for producing chlorine dioxide gas provided in an enclosure comprising an impregnate comprising a chlorine dioxide precursor impregnated in a porous carrier and a proton-generating species, wherein the impregnate and proton-generating species are intermixed to produce a stable mixture and the mixture is provided in an enclosure. The present disclosure also relates to methods for producing chlorine dioxide gas.

25 Claims, 6 Drawing Sheets

Impact of Concentration of Sodium Chlorite, Graphed from Table 4

(56) References Cited

U.S. PATENT DOCUMENTS

| | | |
|---|---|---|
| 4,554,261 A | 11/1985 | Gergely et al. |
| 4,581,219 A | 4/1986 | Imada et al. |
| 4,585,482 A | 4/1986 | Tice et al. |
| 4,590,057 A | 5/1986 | Hicks |
| 4,610,882 A | 9/1986 | Laurent et al. |
| 4,689,169 A | 8/1987 | Mason et al. |
| 4,695,296 A | 9/1987 | Christe |
| 4,731,193 A | 3/1988 | Mason et al. |
| 4,815,092 A | 3/1989 | Chartier |
| 4,844,981 A | 7/1989 | Landau |
| 4,871,701 A | 10/1989 | Danner et al. |
| 4,889,654 A | 12/1989 | Mason et al. |
| 5,008,096 A | 4/1991 | Ringo |
| 5,078,908 A | 1/1992 | Ripley et al. |
| 5,246,622 A | 9/1993 | Shimizu et al. |
| 5,264,227 A | 11/1993 | Laroche et al. |
| 5,278,112 A | 1/1994 | Klatte |
| 5,302,354 A | 4/1994 | Watvedt et al. |
| 5,306,440 A | 4/1994 | Ripley et al. |
| 5,314,852 A | 5/1994 | Klatte |
| 5,346,876 A | 9/1994 | Ichimura et al. |
| 5,360,609 A | 11/1994 | Wellinghoff |
| 5,376,164 A | 12/1994 | Zarchy et al. |
| 5,407,656 A | 4/1995 | Roozdar |
| 5,458,743 A | 10/1995 | Allen |
| 5,464,598 A | 11/1995 | Klatte |
| 5,567,405 A | 10/1996 | Klatte et al. |
| 5,573,743 A * | 11/1996 | Klatte ............... A23K 1/1603 422/29 |
| 5,631,300 A | 5/1997 | Wellinghoff |
| 5,639,295 A * | 6/1997 | Wellinghoff ............ A23B 9/14 106/15.05 |
| 5,668,185 A | 9/1997 | Wellinghoff |
| 5,705,092 A | 1/1998 | Wellinghoff et al. |
| 5,707,739 A | 1/1998 | Wellinghoff et al. |
| 5,730,948 A | 3/1998 | Klatte et al. |
| 5,776,850 A | 7/1998 | Klatte et al. |
| 5,853,689 A | 12/1998 | Klatte |
| 5,855,922 A | 1/1999 | Danner et al. |
| 5,883,739 A | 3/1999 | Ashihara et al. |
| 5,885,543 A | 3/1999 | Klatte |
| 5,974,810 A | 11/1999 | Speronello |
| 5,989,497 A | 11/1999 | Labonte, Jr. |
| 6,077,495 A | 6/2000 | Speronello et al. |
| 6,132,748 A | 10/2000 | Khanna et al. |
| 6,174,508 B1 | 1/2001 | Klatte |
| 6,238,643 B1 | 5/2001 | Thangaraj et al. |
| 6,267,953 B1 | 7/2001 | Bernier et al. |
| 6,284,108 B1 | 9/2001 | DiFrancesco |
| 6,379,643 B1 | 4/2002 | Klatte |
| 6,383,541 B1 | 5/2002 | Danner et al. |
| 6,423,277 B1 | 7/2002 | Gravitt et al. |
| 6,423,289 B1 | 7/2002 | Klatte |
| 6,458,735 B1 | 10/2002 | Klatte |
| 6,503,419 B2 | 1/2003 | Klatte |
| 6,592,919 B1 | 7/2003 | Matthews et al. |
| 6,602,466 B2 | 8/2003 | Hamilton et al. |
| 6,605,558 B2 * | 8/2003 | Klatte ............... C01B 11/023 423/477 |
| 6,607,696 B1 | 8/2003 | Hamilton et al. |
| 6,635,230 B2 | 10/2003 | Klatte |
| 7,220,367 B2 | 5/2007 | Speronello et al. |
| 7,347,994 B2 | 3/2008 | Tenney et al. |
| 7,625,533 B2 | 12/2009 | Doona et al. |
| 7,883,640 B2 | 2/2011 | Doona et al. |
| 7,922,992 B2 | 4/2011 | Ernst et al. |
| 8,622,209 B2 | 1/2014 | Isaac et al. |
| 2001/0036421 A1 | 11/2001 | Speronello et al. |
| 2001/0038805 A1 | 11/2001 | Hamilton et al. |
| 2002/0028191 A1 | 3/2002 | Bernier et al. |
| 2002/0036284 A1 | 3/2002 | Speronello et al. |
| 2002/0056830 A1 | 5/2002 | Klatte |
| 2002/0122854 A1 | 9/2002 | Danner et al. |
| 2003/0021819 A1 | 1/2003 | Khanna et al. |
| 2003/0082087 A1 | 5/2003 | Klatte |
| 2004/0051080 A1 | 3/2004 | Ernst et al. |
| 2006/0099121 A1 | 5/2006 | Doona et al. |
| 2007/0081919 A1 | 4/2007 | Koermer et al. |
| 2014/0086821 A1 * | 3/2014 | Ozawa ............... C01B 11/024 423/477 |

FOREIGN PATENT DOCUMENTS

| | | |
|---|---|---|
| JP | 56067521 | 6/1981 |
| JP | 58-161904 | 9/1983 |
| JP | 60000827 | 1/1985 |
| JP | 61256915 | 11/1986 |
| JP | 01071804 | 3/1989 |
| JP | 2198629 | 8/1990 |
| JP | 03000979 | 1/1991 |
| JP | 6-285368 | 10/1994 |
| JP | 3023863 | 3/2000 |
| WO | 8505008 | 11/1985 |
| WO | 8505038 | 11/1985 |
| WO | 9811776 | 3/1998 |
| WO | 9838865 | 9/1998 |
| WO | 0010695 | 3/2000 |
| WO | 0065910 | 11/2000 |
| WO | 0069775 | 11/2000 |
| WO | 03051407 | 6/2003 |
| WO | 2011097224 | 8/2011 |

OTHER PUBLICATIONS

Gao et al., Use of Tailored Zeolites for Removal of Benzene and Toluene From Water, 45th Purdue Industrial Waste Conference Proceedings, 1991, pp. 509-516, Lewis Publishers, Inc., Chelsea, Michigan.

Masschelein, Chlorine Dioxide-Chemistry and Environmental Impact of Oxychlorine Compounds, Industrial Synthesis, (1979) (Ann Arbor Science Publishers Inc., Ann Arbor, Michigan), pp. 138-141.

Morita et al., Manufacture of a Solid Chlorine Dioxide Generating Agent, Chemical Abstracts, vol. 100, No. 2, Abstract No. 9463, Jan. 9, 1984.

* cited by examiner

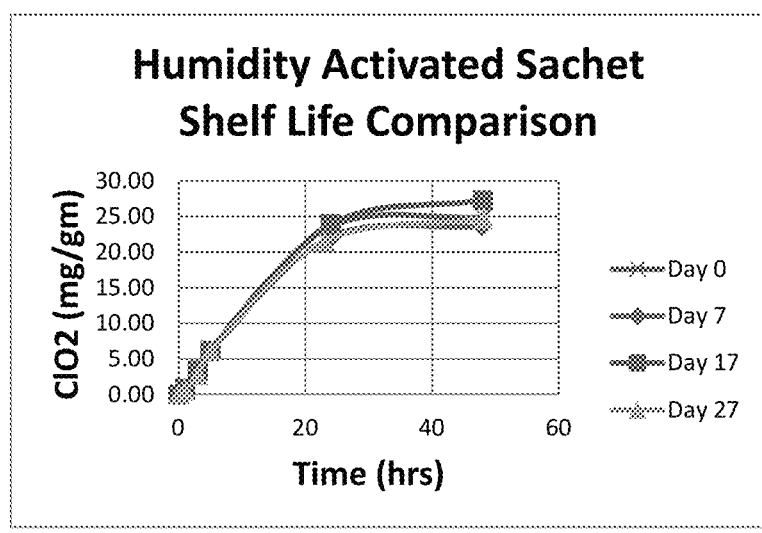
Figure 1. Chlorine Dioxide Gas Production Over Time, Graphed from Table 1

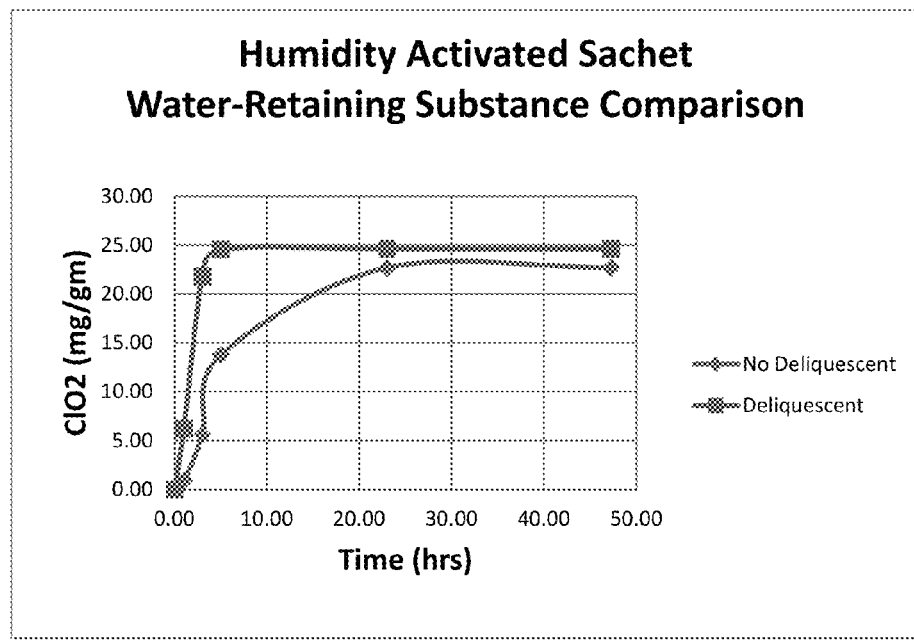
Figure 2: Impact of Using a Water-Retaining Substance, Graphed from Table 2

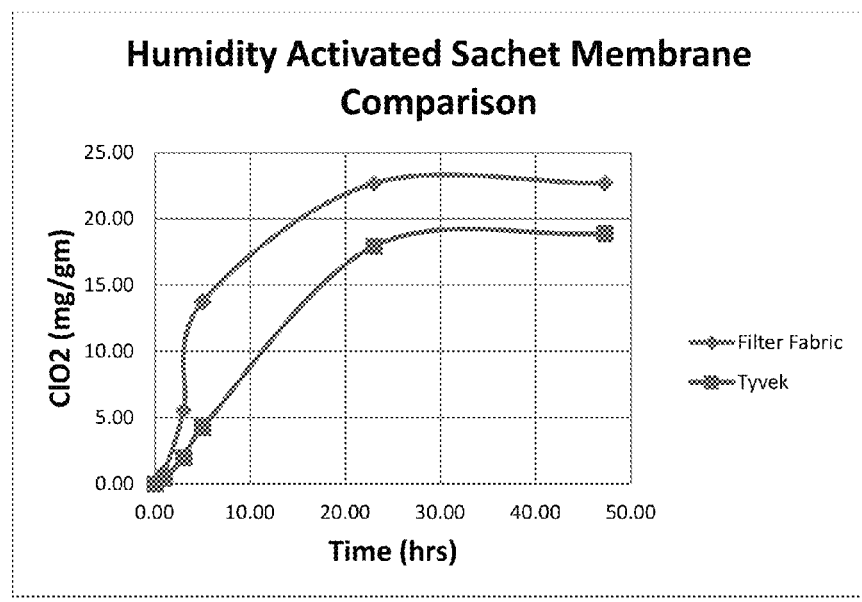
Figure 3: Impact of Using Different Membrane Materials, Graphed from Table 3

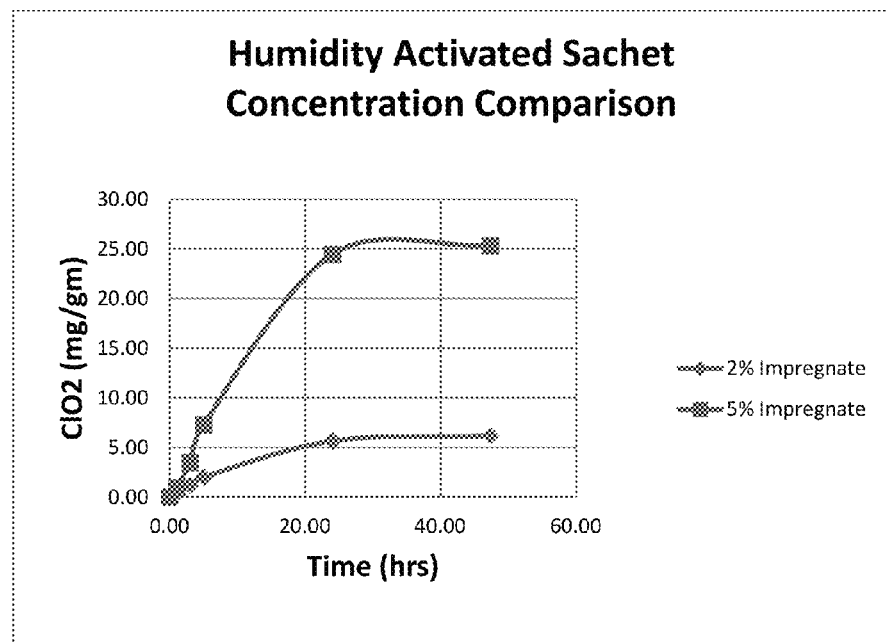
Figure 4. Impact of Concentration of Sodium Chlorite, Graphed from Table 4

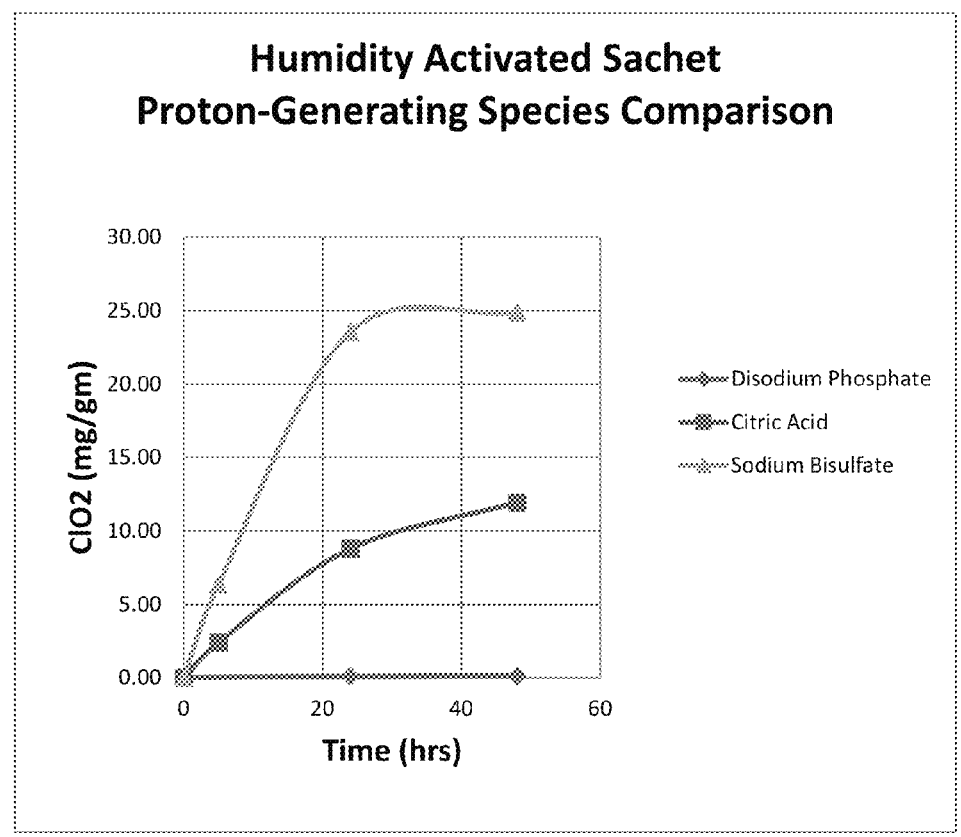
Figure 5: Impact of Choice of Proton-Generating Species, Graphed from Table 5

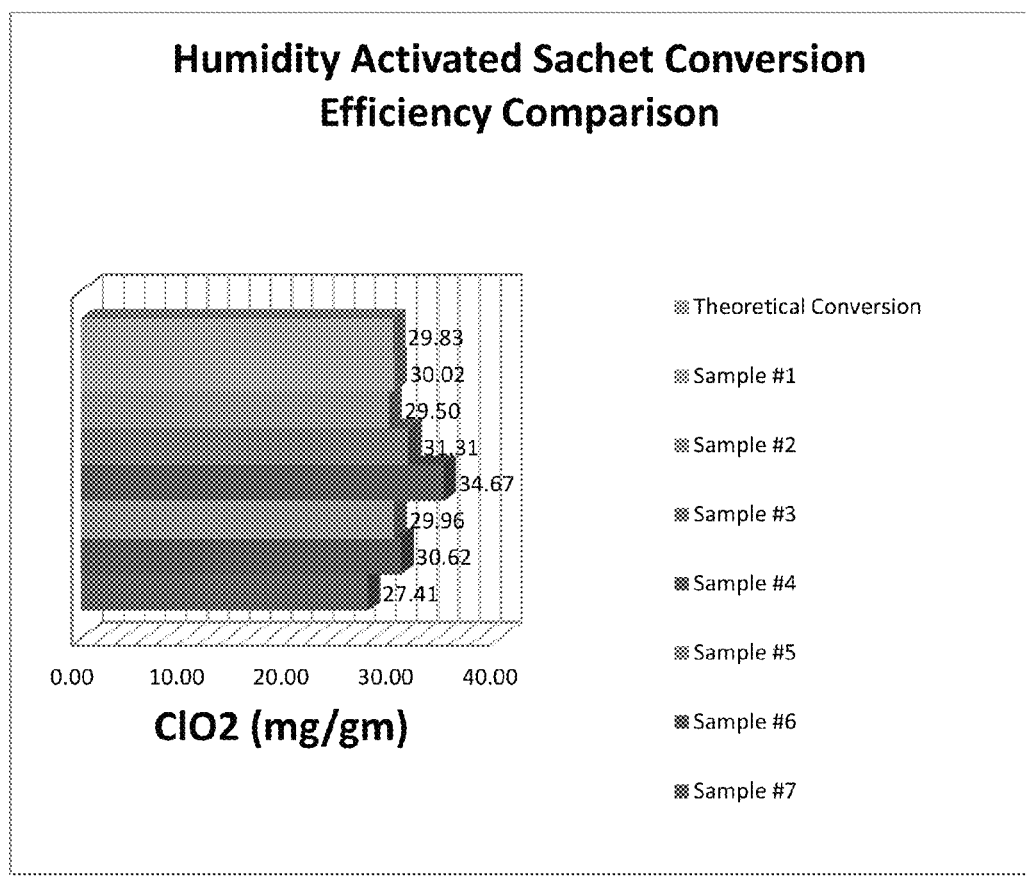
Figure 6. Comparison of Conversion Efficiency, Graphed from Table 6

MIXTURES FOR PRODUCING CHLORINE DIOXIDE GAS IN ENCLOSURES AND METHODS OF MAKING THE SAME

CROSS-REFERENCE TO RELATED APPLICATIONS

This application claims the benefit of priority to U.S. Provisional Patent Application No. 61/750,965 filed Jan. 10, 2013, the disclosure of which is incorporated herein by reference in its entirety.

FIELD OF THE DISCLOSURE

The present disclosure relates to a mixture for producing chlorine dioxide gas provided in an enclosure comprising an impregnate comprising a chlorine dioxide precursor impregnated in a porous carrier and a proton-generating species, wherein the impregnate and proton-generating species are intermixed to produce a mixture and the mixture is provided in an enclosure. The present disclosure also relates to methods for producing chlorine dioxide gas.

BACKGROUND

Chlorine dioxide gas is useful for food preservation, laboratory research, disinfecting drinking water and a variety of other applications. There is a need in the art to provide a composition for producing chlorine dioxide gas that remains stable during storage at varied storage times until it is ready to be used to produce chlorine dioxide and exposed to environmental humidity. Furthermore, there is a need in the art to provide a composition for producing chlorine dioxide gas that provides consistent production of chlorine dioxide regardless of the relative humidity it is exposed to after storage.

SUMMARY OF THE DISCLOSURE

The present disclosure relates to a mixture for producing chlorine dioxide gas provided in an enclosure comprising an impregnate comprising a chlorine dioxide precursor (e.g., metal chlorites, metal chlorates, chloric acid, and hypochlorous acid) impregnated in a porous carrier (e.g., zeolite, diatomaceous earth, silica, alumina, porous polymer, clay, or a mixture thereof) and a proton-generating species (e.g., an organic acid, an inorganic acid, or a salt thereof), wherein the impregnate and proton-generating species are intermixed to produce a stable mixture and the mixture is provided in an enclosure. In some embodiments, the amount of chlorine dioxide gas produced in 24 hours when the enclosure is opened after 27 days of storage is 90% or greater of the amount of chlorine dioxide produced in 24 hours when the enclosure is opened after 0 days of storage. In some embodiments, the amount of chlorine dioxide produced in 24 hours when the enclosure is open and exposed to a temperature of 70° F. and 50% relative humidity (% RH) is 90% or greater of the amount of chlorine dioxide gas produced in 24 hours when the enclosure is opened and exposed to a temperature of 70° F. and 99% RH. In some embodiments, the amount of chlorine dioxide produced in 24 hours when the enclosure is opened and exposed to a temperature of 70° F. and 35% RH is 85% or greater or 90% or greater of the amount of chlorine dioxide produced in 24 hours when the enclosure is opened and exposed to a temperature of 70° F. and 99% RH.

In some embodiments, the impregnate is dried to 5% water or less. In some embodiments, the impregnate is treated with a base (e.g., potassium hydroxide, sodium hydroxide, calcium hydroxide, or a blend thereof). In some embodiments, the mixture further comprises a water-retaining substance (e.g., calcium chloride, magnesium sulfate, potassium chloride, and mixtures thereof). In some embodiments, the water-retaining substance is impregnated in a porous carrier. In some embodiments, the proton-generating species is provided in excess of the stoichiometric amount. In some embodiments, the proton-generating species is impregnated in a porous carrier. In some embodiments, the enclosure is a humidity-activated sachet and the mixture is enclosed within a membrane (e.g., a polyethylene or paper filter).

The present disclosure also relates to methods of producing chlorine dioxide gas by providing a mixture disclosed herein in an enclosure and opening the enclosure. The present disclosure also relates to methods of limiting the production of bio-organisms in a food package by providing a mixture disclosed herein in an enclosure.

BRIEF DESCRIPTION OF THE FIGURES

FIG. 1 depicts a graph of the shelf-life comparison data of Table 1, shown in the examples.

FIG. 2 depicts a graph of the water-retaining substance comparison data of Table 2, shown in the examples.

FIG. 3 depicts a graph of the membrane comparison data of Table 3, shown in the examples.

FIG. 4 depicts a graph of the sodium chlorite concentration comparison data of Table 4, shown in the examples.

FIG. 5 depicts a graph of the proton-generating species comparison data of Table 5, shown in the examples.

FIG. 6 depicts a graph of the conversion efficiency comparison data of Table 6, shown in the examples.

DETAILED DESCRIPTION

The present disclosure includes methods and compositions for producing chlorine dioxide that is based on chlorine dioxide precursors that react with protons to produce chlorine dioxide.

The chlorine dioxide precursor can be chosen from any composition capable of producing chlorine dioxide gas when mixed with a proton-generating species. In some embodiments, the chlorine dioxide precursor includes a metal chlorite, metal chlorate, chloric acid, hypochlorous acid, or mixtures thereof. In some embodiments, the metal chlorites and chlorates are in the form of alkali metal or alkaline earth metal chlorites and chlorates. Exemplary metal chlorites include, but are not limited to, sodium chlorite, barium chlorite, calcium chlorite, lithium chlorite, potassium chlorite, magnesium chlorite, and mixtures thereof. Exemplary metal chlorates include, but are not limited to, sodium chlorate, lithium chlorate, potassium chlorate, magnesium chlorate, barium chlorate, and mixtures thereof.

The chlorine dioxide precursor can be provided in any form that allows it to react with protons to produce chlorine dioxide. In some embodiments, the chlorine dioxide precursor is in the form of a powder. In some embodiments, the chlorine dioxide precursor is provided in an aqueous solution. In some embodiments, the chlorine dioxide precursor is impregnated in a porous carrier. In some embodiments, the porous carrier is inert. In some embodiments, the porous carrier has pores, channels, or the like located therein. Exemplary porous carriers include, but are not limited to, silica, pumice, diatomaceous earth, bentonite, clay, porous polymer, alumina, zeolite (e.g., zeolite crystals), or mixtures thereof. In some embodiments, the porous carrier can have a particle size of from 0.02 mm to 1 inch (e.g., 0.125 inch, 0.25 inch, 0.50 inch, or 0.75 inch), in their largest dimension. In some embodiments, the porous carrier can have dimensions substantially equal to 0.25 inch by 0.167 inch, 0.125 inch by 0.10 inch, 0.25 inch by 0.125 inch, 0.125 inch by 0.50 inch, or 0.50 inch by 0.75 inch. In some embodiments, the porous carrier is uniformly impregnated throughout the volume of the porous carrier via the pores, channels, and the like, with the at least one chlorine dioxide precursor.

In some embodiments, the porous carrier is impregnated with the chlorine dioxide precursor by using a porous carrier that has a low moisture content. In some embodiments, the low moisture content is 5% or less (e.g., 4% or less, 3% or less, 2% or less, or 1% or less) by weight. In some embodiments, the porous carrier has an initial moisture content above 5% and thus can be dehydrated to produce a moisture content of 5% or less. In some embodiments, the dehydrated porous carrier is then immersed in or sprayed with an aqueous solution of the chlorine dioxide precursor at an elevated temperature (e.g., in the range from 120° F. to 190° F.) and the resulting slurry is thoroughly mixed. In some embodiments, the mixed slurry is then air-dried to a moisture level of from 0% to 20% (e.g., from 2% to 18%, from 4% to 16%, from 6% to 14%, from 8% to 12%) by weight to produce the impregnate (i.e., chlorine dioxide precursor impregnated in a porous carrier) disclosed herein. In some embodiments, the impregnate disclosed herein can be prepared without a drying step by calculating the amount of the aqueous solution of the chlorine dioxide precursor needed to achieve the desired final moisture level (e.g., from 0% to 20%, from 2% to 18%, from 4% to 16%, from 6% to 14%, from 8% to 12% by weight) and adding this amount of the aqueous solution to the dehydrated porous carrier to impregnate the porous carrier. In some embodiments, the porous carrier include from 1% to 50% chlorine dioxide precursor (e.g., from 5% to 45%, from 1% to 35%, from 10% to 30%), from 0% to 20% water (e.g., 15% or less, 10% or less, 5% or less), and from 50% to 98.5% porous carrier (e.g., from 55% to 95%, from 60% to 90%, from 65% to 85%) by weight. In some embodiments, the porous carrier can include from 1% to 35% chlorine dioxide precursor, less than 5% water, and from 65% to 94.5% porous carrier by weight. In some embodiments, the chlorine dioxide is impregnated in zeolite crystals as described above and as described in U.S. Pat. Nos. 5,567,405; 5,573,743; 5,730,948; 5,776,850; 5,853,689; 5,885,543; 6,174,508; 6,379,643; 6,423,289; 7,347,994; and 7,922,992, which are incorporated by reference in their entirety.

In some embodiments, the chlorine dioxide precursor is impregnated into a porous carrier and treated with a base. In some embodiments, the base is any suitable base that can reduce the available protons and inhibit the reaction until the proton-generating species overcomes the base and reacts with the chlorine dioxide precursor, to enhance shelf stability and slow the reaction rate once the mixture is activated. Exemplary bases include, but are not limited to, potassium hydroxide, sodium hydroxide, calcium hydroxide, or a blend thereof.

In addition to the chlorine dioxide precursor, the mixtures disclosed herein can include a water-retaining substance. In some embodiments, the water-retaining substance is a deliquescent or other compound capable of absorbing or retaining either liquid water or water vapor from air or other moisture-containing fluids. Exemplary water-retaining substances include, but are not limited to, calcium chloride, magnesium sulfate, potassium chloride, potassium hydroxide, and mixtures thereof. The water-retaining substance can be provided in any form that allows it to retain liquid water, water vapor from air, or other moisture-containing fluids. In some embodiments, the water-retaining substance is in the form of a powder. In some embodiments, the water-retaining substance is provided in an aqueous solution. In some embodiments, the water-retaining substance is impregnated in a porous carrier. In some embodiments, the porous carrier is inert. In some embodiments, the porous carrier has pores, channels, or the like located therein. Exemplary porous carriers include, but are not limited to, silica, pumice, diatomaceous earth, bentonite, clay, porous polymer, alumina, zeolite (e.g., zeolite crystals), or mixtures thereof. In some embodiments, the porous carrier can have a particle size of from 0.02 mm to 1 inch (e.g., 0.125 inch, 0.25 inch, 0.50 inch, or 0.75 inch), in their largest dimension. In some embodiments, the porous carrier can have dimensions substantially equal to 0.25 inch by 0.167 inch, 0.125 inch by 0.10 inch, 0.25 inch by 0.125 inch, 0.125 inch by 0.50 inch, or 0.50 inch by 0.75 inch. In some embodiments, the porous carrier is uniformly impregnated throughout the volume of the porous carrier via the pores, channels, and the like, with the at least one water-retaining substance.

In some embodiments, the porous carrier is impregnated with the water-retaining substance by using a porous carrier that has a low moisture content. In some embodiments, the low moisture content is 5% or less (e.g., 4% or less, 3% or less, 2% or less, or 1% or less) by weight. In some embodiments, the porous carrier has an initial moisture content above 5% and thus can be dehydrated to produce a moisture content of 5% or less. In some embodiments, the dehydrated porous carrier is then immersed in or sprayed with an aqueous solution of the chlorine dioxide precursor at an elevated temperature (e.g., in the range from 120° F. to 190° F.) and the resulting slurry is thoroughly mixed. In some embodiments, the mixed slurry is then air-dried to a moisture level of from 0% to 20% (e.g., from 2% to 18%, from 4% to 16%, from 6% to 14%, from 8% to 12%) by weight to produce an impregnate (i.e., chlorine dioxide precursor impregnated in a porous carrier), which may also include the water-retaining substance. In some embodiments, the impregnate disclosed herein can be prepared without a drying step by calculating the amount of the aqueous solution of the chlorine dioxide precursor and/or water-retaining substance needed to achieve the desired final moisture level (e.g., from 0% to 20%, from 2% to 18%, from 4% to 16%, from 6% to 14%, from 8% to 12% by weight) and adding this amount of the aqueous solution to the dehydrated porous carrier to impregnate the porous carrier. In some embodiments, the porous carrier include from 1% to 50% chlorine dioxide precursor (e.g., from 5% to 45%, from 1% to 35%, from 10% to 30%), from 0% to 15% water-retaining substance (e.g., 12% or less, 10% or less, 8% or less, 6% or less, 4% or less, 2% or less), from 0% to 20% water (e.g., 15% or less, 10% or less, 5% or less), and from 50% to 98.5% porous carrier (e.g., from 55% to 95%, from 60% to 90%, from 65% to 85%) by weight. In some embodiments, the porous carrier can include from 1% to 35% chlorine dioxide precursor, from 1% to 8% water-retaining substance, less than 5% water, and from 65% to 94.5% porous carrier by weight.

In some embodiments, the porous carrier impregnated with the chlorine dioxide precursor can also be impregnated with the water-retaining substance, for instance, through the use of an aqueous solution containing both the chlorine dioxide precursor and the water-retaining substance. In some embodiments, a porous carrier separate from the porous carrier containing the chlorine dioxide precursor can be provided that is impregnated with the water-retaining substance and can be prepared in the manner described above. The water-retaining substance can be provided in any amount that controls the rate of release of chlorine dioxide by controlling the rate at which protons are produced, e.g., by a proton-generating species as discussed below, and thus can control the rate at which chlorine dioxide is produced. In some embodiments, the rate at which the chlorine dioxide is produced can, for example, be controlled by varying the relative amounts by weight of the chlorine dioxide precursor and the water-retaining substance.

A proton-generating species as disclosed herein can be any composition capable of generating protons to react with the chlorine dioxide precursor. In some embodiments, the proton-generating species is an inorganic acid, an organic acid, or a salt thereof. In some embodiments, the proton-generating species is in the form of an aqueous acid or a metal salt. Exemplary acids include, but are not limited to, acetic acid, citric acid, phosphoric acid, hydrochloric acid, propionic acid, sulfuric acid, and mixtures thereof. In some embodiments, proton-generating species comprises a metal salt. In some embodiments, the metal salt is a chloride, sulfate, phosphate, propionate, acetate, or citrate that combines with water to produce an acid, i.e., protons. In some embodiments, the metal is an alkali metal, alkaline earth metal, or a transition metal. Exemplary metal salts include, but are not limited to, ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, sodium citrate, sodium sulfate, sodium bisulfate, hydrogen phosphate, disodium hydrogen phosphate, and mixtures thereof. In some embodiments, the proton-generating species is a metal salt that can also act as a water-retaining substance (e.g., $CaCl_2$, $MgSO_4$). In some embodiments, the acid is provided in the form of zeolite crystals impregnated with the acid and are produced by any suitable method.

In some embodiments, the proton-generating species is activated to produce protons by contacting the proton-generating species with a moisture-containing (or water-containing) fluid. In some embodiments, the metal salt is ferric chloride, ferric sulfate, or a mixture thereof, and these iron salts can absorb water in addition to functioning as a proton-generating species. In some embodiments, the moisture-containing fluid is liquid water or an aqueous solution. In some embodiments, the moisture-containing fluid is a moisture-containing gas such as air or water vapor. In some embodiments, the protons produced by the proton-generating species react with the chlorine dioxide precursor to produce chlorine dioxide. The proton-generating species can also be activated other than by exposure to a moisture-containing fluid. In some embodiments, the proton-generating species can be activated and can release protons upon exposure to the water in the powders or impregnated porous carrier containing the chlorine dioxide precursor.

The proton-generating species can be provided in any form that allows the release of protons. In some embodiments, the proton-generating species is in the form of a liquid. In some embodiments, the proton-generating species is in the form of a powder. In some embodiments, the proton-generating species is provided in an aqueous solution. In some embodiments, the proton-generating species is impregnated in a porous carrier. In some embodiments, the porous carrier is inert. In some embodiments, the porous carrier has pores, channels, or the like located therein. Exemplary porous carriers include, but are not limited to, silica, pumice, diatomaceous earth, bentonite, clay, porous polymer, alumina, zeolite (e.g., zeolite crystals), or mixtures thereof. In some embodiments, the porous carrier can have a particle size of from 0.02 mm to 1 inch (e.g., 0.125 inch, 0.25 inch, 0.50 inch, or 0.75 inch), in their largest dimension. In some embodiments, the porous carrier can have dimensions substantially equal to 0.25 inch by 0.167 inch, 0.125 inch by 0.10 inch, 0.25 inch by 0.125 inch, 0.125 inch by 0.50 inch, or 0.50 inch by 0.75 inch.

In some embodiments, the porous carrier is uniformly impregnated throughout the volume of the porous carrier via the pores, channels, and the like, with the at least one proton-generating species.

In some embodiments, the porous carrier is impregnated with the proton-generating species by using a porous carrier that has a low moisture content. In some embodiments, the low moisture content is 5% or less (e.g., 4% or less, 3% or less, 2% or less, or 1% or less) by weight. In some embodiments, the porous carrier has an initial moisture content above 5% and thus can be dehydrated to produce a moisture content of 5% or less. In some embodiments, the dehydrated porous carrier is then immersed in or sprayed with an aqueous solution of the proton-generating species at an elevated temperature (e.g., in the range from 120° F. to 190° F.) and the resulting slurry is thoroughly mixed. In some embodiments, the mixed slurry is then air-dried to a moisture level of from 0% to 20% (e.g., from 2% to 18%, from 4% to 16%, from 6% to 14%, from 8% to 12%) by weight to produce an impregnate (i.e., proton-generating species impregnated in a porous carrier). In some embodiments, the impregnate disclosed herein can be prepared without a drying step by calculating the amount of the aqueous solution of the proton-generating species needed to achieve the desired final moisture level (e.g., from 0% to 20%, from 2% to 18%, from 4% to 16%, from 6% to 14%, from 8% to 12% by weight) and adding this amount of the aqueous solution to the dehydrated porous carrier to impregnate the porous carrier. In some embodiments, the porous carrier include from 1% to 50% proton-generating species (e.g., from 5% to 45%, from 1% to 35%, from 10% to 30%), from 0% to 20% water (e.g., 15% or less, 10% or less, 5% or less), and from 50% to 98.5% porous carrier (e.g., from 55% to 95%, from 60% to 90%, from 65% to 85%) by weight. In some embodiments, the proton-generating species is provided in excess of the stoichiometric amount required to produce chlorine dioxide gas when reacting with the chlorine dioxide precursor.

In some embodiments, the porous carrier impregnated with the proton-generating species is separate from the porous carrier that is impregnated with the chlorine dioxide precursor. In some embodiments, the porous carrier impregnated with the proton-generating species is separate from the porous carrier that is impregnated with the chlorine dioxide precursor and is separate from the porous carrier that is impregnated with the water-retaining substance. In some embodiments, the porous carrier impregnated with the proton-generating species is separate from the porous carrier that is impregnated with the chlorine dioxide precursor and water-retaining substance. In some embodiments, zeolite crystals are formed through the use of an aqueous solution of the proton-generating species in the manner described above with respect to the chlorine dioxide precursor.

The proton-generating species (whether impregnated in a porous carrier or not) and the chlorine dioxide precursor (whether impregnated in a porous carrier or not) can be mixed or otherwise combined. In some embodiments, the mixture is sprayed or coated on a surface. In some embodiments, the mixture is absorbed into a material such as a sponge, pad, mat, or the like. In some embodiments, the mixture can be placed in a reservoir, container, box, sachet, or the like.

In some embodiments, the proton-generating species is provided in the same enclosure with an impregnate comprising the chlorine dioxide precursor impregnated in a porous carrier. In some embodiments, the enclosing material can include any enclosing material that is substantially impervious to liquid water. In some embodiments, the mixture is placed in a humidity-activated sachet and enclosed within an enclosing material such as a membrane. Exemplary membranes include, but are not limited to, a polyethylene or paper filter. Exemplary commercially available enclosing materials include, but are not limited to, TYVEK® and GORTEX®. In some embodiments, the enclosing material allows water vapor to enter the enclosure. In some embodiments, the enclosing material allows chlorine dioxide gas to be released from the enclosure and enter the atmosphere. In some embodiments, the enclosing material is a sachet comprising three layers of membrane material forming a two-compartment sachet to separate the proton-generating species (whether impregnated in a porous carrier or not) from the chlorine dioxide precursor (whether impregnated in a porous carrier or not). In some embodiments, the multiple layers of membrane material can be chosen from different membrane materials, wherein the permeability of the outer membrane can determine how fast humidity can enter the sachet to activate the precursor and the proton-generating species. In some embodiments, the multiple layers of membrane material can be chosen from different membrane materials, wherein the center membrane can determine how fast the protons from the proton-generating source can pass to the precursor to react and generate chlorine dioxide.

In some embodiments, the system comprising the mixture and the enclosure is scalable for the production of chlorine dioxide. In some embodiments, the system is configured to produce milligrams of chlorine dioxide. In some embodiments, the system is configured to produce several hundred grams of chlorine dioxide. In some embodiments, the system is configured to produce kilograms of chlorine dioxide.

Chlorine dioxide gas can be produced, for instance, by contacting the mixture with a source of humidity. In some embodiments, the mixture is in an enclosure disclosed herein, wherein the mixture produces chlorine dioxide gas when the enclosure is opened.

In some embodiments, the proton-generating species and chlorine dioxide precursor are provided in the same package, while maintaining stability during storage until exposed to and activated by a source of humidity. In some embodiments, the rate of reaction and the release of chlorine dioxide are controlled by factors including, but not limited to, choice of chlorine dioxide precursor, choice of proton-generating source, whether the chlorine dioxide precursor is impregnated into a porous carrier, whether the proton-generating source is impregnated into a porous carrier, use of a water-retaining substance, physical properties of the porous carrier, enclosure membrane properties, and combinations thereof. In some embodiments, the rate of reaction is varied through choosing the physical properties of the porous carrier including, but not limited to, particle size, pore diameter, dilution of the relative particle mixture with inert properties.

In some embodiments, the rate of reaction and the release of chlorine dioxide are controlled by any factor capable of controlling the influx of humidity into the package. In some embodiments, the enclosure material is any material capable of allowing chlorine dioxide gas to escape at a desired rate.

The chlorine dioxide producing composition is stable during storage such that it maintains its ability to produce chlorine dioxide after a period of storage time. In some embodiments, the amount of chlorine dioxide produced in 24 hours when the enclosure is opened after 27 days of storage is 90% or greater (e.g., 91% or greater, 92% or greater, 93% or greater, 94% or greater, 95% or greater, 96% or greater, 97% or greater, 98% or greater, or 99% or greater) of the amount of chlorine dioxide produced in 24 hours when the enclosure is opened after 0 days of storage. In some embodiments, the amount of chlorine dioxide produced in 48 hours when the enclosure is opened after 27 days of storage is 90% or greater (e.g., 91% or greater, 92% or greater, 93% or greater, 94% or greater, 95% or greater, 96% or greater, 97% or greater, 98% or greater, or 99% or greater) of the amount of chlorine dioxide produced in 48 hours when the enclosure is opened after 0 days of storage.

The chlorine dioxide producing composition can produce chlorine dioxide at similar rates regardless of the humidity it is exposed to after it is removed from its storage enclosure. In some embodiments, the amount of chlorine dioxide produced in 24 hours when the enclosure is open and exposed to a temperature of 70° F. and 50% relative humidity (% RH) is 90% or greater (e.g., 91% or greater, 92% or greater, 93% or greater, 94% or greater, 95% or greater, 96% or greater, 97% or greater, 98% or greater, or 99% or greater) of the amount of chlorine dioxide gas produced in 24 hours when the enclosure is opened and exposed to a temperature of 70° F. and 99% RH. In some embodiments, the amount of chlorine dioxide produced in 24 hours when the enclosure is open and exposed to a temperature of 70° F. and 35% relative humidity (% RH) is 85% or greater (e.g., 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater) of the amount of chlorine dioxide gas produced in 24 hours when the enclosure is opened and exposed to a temperature of 70° F. and 99% RH.

In some embodiments, the chlorine dioxide producing composition can be provided in food packaging, for example, in a sachet. The composition can be used to control food spoilage and destroy food safety pathogens on food products in a variety of foods including meats, vegetables, fruits, grains, nuts, and mixtures thereof. In some embodiments, the composition is provided in a food package that includes a fruit, a vegetable, or a mixture thereof.

The chlorine dioxide gas can also be useful, for instance, for killing biological contaminants (such as bio-organisms, mold, fungi, yeast, and bacteria) and for oxidizing volatile organic chemicals that can contaminate fluid. In some embodiments, the system is highly portable. In some embodiments, the system is simple to use, allowing minimally trained personnel to use the produce in a wide variety of applications including, but not limited to, eliminating odor, sterilizing medical devices, decontaminating systems, and neutralizing chemical and biological threats.

The disclosures herein can be used for a variety of additional applications involving solid, liquid, and/or gaseous environments. Exemplary uses for chlorine dioxide gas include, but are not limited to, treating solids such as those having metal surfaces, wood surfaces, plastic surfaces, fabric surfaces, or combinations thereof. Further exemplary uses for chlorine dioxide gas include, but are not limited to, uses for animal waste, pet and livestock litters; medical devices including bandages, ostomy devices and medical instruments; fabric items including drapes, wall hangings, upholstery, and clothing. Exemplary liquids that can be treated with chlorine dioxide gas include, but are not limited to, liquid waste and water including potable water. Exemplary gaseous environments that can be treated with chlorine dioxide gas include, but are not limited to, those containing noxious and/or objectionable gases such as animal environments, smoke-laden environments (e.g., tobacco smoke), and exhaust systems from noxious gas producing facilities (e.g., chemical plants). Another exemplary use for chlorine dioxide gas includes, but is not limited to, use in ice machines to prevent incorporation of unwanted substances into the ice.

By way of non-limiting illustration, examples of certain embodiments of the present disclosure are given below.

EXAMPLES

In the examples provided below, diatomaceous earth was impregnated with sodium chlorite. The final concentration of the sodium chlorite in the impregnate was 5% by weight. The final concentration of calcium chloride in the impregnate was 5% by weight. The impregnate was combined in equal parts by weight with the sodium bisulfate, citric acid, or disodium hydrogen phosphate and placed in packages made of Dupont 1073B TYVEK or Glatfelter membrane (filter paper/membrane) SS-H-121/8/C. The packages were sealed in poly bags to protect them from humidity for 0 days to 27 days. Samples were removed at varying time points and profiled for chlorine dioxide gas production over time, ranging up to 48 hours, as shown in Table 1 and graphed in FIG. 1.

TABLE 1

Chlorine Dioxide Gas Production over Time
Humidity Activated Sachet - Shelf-Life Comparison

| | Time (Hrs) | | | | |
|---|---|---|---|---|---|
| | 0 | 1 | 3 | 5 | 24 | 48 |
| Chlorine Dioxide (mg ClO$_2$/gram impregnate) | | | | | |
| Day 0 | 0 | 1.05 | 3.51 | 6.34 | 23.55 | 24.88 |
| Day 7 | 0 | 0.87 | N/A | 6.00 | 22.07 | 23.62 |
| Day 17 | 0 | 0.83 | 3.37 | 6.14 | 23.90 | 27.27 |
| Day 27 | 0 | 0.58 | 2.75 | 6.05 | 21.52 | 24.67 |

Samples were humidified by placing them over 5% potassium iodide solution to collect the chlorine dioxide as it was produced (relative humidity >90%). The amount of chlorine dioxide produced was determined by dual neutral/acid titration—a procedure taken from Standard Methods 14$^{th}$ Edition, *Iodometric Method for Determination of Chlorine Dioxide, Chlorite and Chlorine*. Samples placed in a sachet and suspended over potassium iodide solution without a proton source did not produce any detectable chlorine dioxide after 5 days of exposure and capture.

The impregnate was combined with calcium chloride to observe the change the rate of reaction by changing the availability of humidity to initiate the reaction. Samples were removed at varying time points and profiled for chlorine dioxide gas production over time, ranging up to 48 hours, as shown in Table 2 and graphed in FIG. 2.

TABLE 2

Impact of Using a Water-Retaining Substance
Humidity Activated Sachet - Water-Retaining Substance Comparison

| | Time (Hrs) | | | | |
|---|---|---|---|---|---|
| | 0 | 1 | 3 | 5 | 23 | 48 |
| Chlorine Dioxide (mg ClO$_2$/gram impregnate) | | | | | |
| No Deliquescent | 0 | 0.91 | 5.56 | 13.74 | 22.68 | 22.68 |
| Deliquescent | 0 | 6.22 | 21.77 | 24.55 | 24.62 | 24.62 |

The sachet system was constructed with differing membranes, which can regulate the rate of influx of humidity and change the reaction rate through differing permeability of the sachet. A comparison of the chlorine dioxide production when using a Glatfelter membrane (filter paper/membrane) and TYVEK® is reflected in Table 3 and FIG. 3.

TABLE 3

Impact of Using Different Membranes
Humidity Activated Sachet - Membrane Comparison

| | Time (Hrs) | | | | |
|---|---|---|---|---|---|
| | 0 | 1 | 3 | 5 | 23 | 48 |
| Chlorine Dioxide (mg ClO$_2$/gram impregnate) | | | | | |
| Glatfelter membrane (filter paper/membrane) | 0 | 0.91 | 5.56 | 13.74 | 22.68 | 22.68 |
| TYVEK | 0 | 0.44 | 1.98 | 4.27 | 17.93 | 18.89 |

The rate of the reaction was modified by adjusting the chemical concentrations of sodium chlorite in the diatomaceous earth, the results of which are shown in Table 4 and FIG. 4.

TABLE 4

Impact of Concentration of Sodium Chlorite.
Humidity Activated Sachet - Concentration Comparison

| | Time (Hrs) | | | | |
|---|---|---|---|---|---|
| | 0 | 1 | 3 | 5 | 23 | 48 |
| Chlorine Dioxide (mg ClO$_2$/gram impregnate) | | | | | |
| 2% Imp | 0 | 0.41 | 1.21 | 2.01 | 5.65 | 6.19 |
| 5% Imp | 0 | 0.91 | 3.46 | 7.30 | 24.44 | 25.33 |

The rate of the reaction was modified using various proton-generating species. The impact of using different proton-generating species is reflected in Table 5 and FIG. 5.

TABLE 5

Impact of Choice of Proton-Generating Species
Humidity Activated Sachet - Proton Donor Comparison

| Time (Hrs) | 0 | 5 | 24 | 48 |
|---|---|---|---|---|
| Chlorine Dioxide (mg ClO$_2$/gram impregnate) | | | | |
| Disodium phosphate | 0.00 | n/a | 0.09 | 0.14 |
| Citric Acid | 0.00 | 2.39 | 8.79 | 11.92 |
| Sodium Bisulfate | 0.00 | 6.34 | 23.55 | 24.88 |

The system was found to be highly efficient at converting the chlorine dioxide precursor to chlorine dioxide (e.g., exceeding 90% of the theoretical conversion, approaching 100% of the theoretical conversion). The theoretical 100% conversion of sodium chlorite produces 597 milligrams of chlorine dioxide for each gram of pure sodium chlorite. Seven samples having 5% sodium chlorite impregnated into diatomaceous earth were measured for their conversion efficiency, as reflected in Table 6 and FIG. 6.

TABLE 6

Comparison of Conversion Efficiency
Humidity Activated Sachet - Conversion Efficiency Comparison

| 5% chlorite impregnate by weight | Theoretical Conversion (mg/gm) Actual Conversion (mg/gm) | 29.83 % Conversion |
|---|---|---|
| Sample #1 | 30.02 | 101% |
| Sample #2 | 29.50 | 99% |

TABLE 6-continued

Comparison of Conversion Efficiency
Humidity Activated Sachet - Conversion Efficiency Comparison

| 5% chlorite impregnate by weight | Theoretical Conversion (mg/gm) Actual Conversion (mg/gm) | 29.83 % Conversion |
|---|---|---|
| Sample #3 | 31.31 | 105% |
| Sample #4 | 34.67 | 116% |
| Sample #5 | 29.96 | 100% |
| Sample #6 | 30.62 | 103% |
| Sample #7 | 27.41 | 92% |

Effect of Storage on Reactivity of Media

Sachets were suspended in containers at 70° F. over 5% potassium iodide (KI) solution (99% RH) for 24 hours then moved to fresh containers at 70° F. over 5% KI solution (99% RH) for 24 additional hours. Each KI solution was titrated using Standard Methods Iodometric Titration technique to determine the $ClO_2$ concentration at each time point. Results for each sample were totaled to determine 48 hour $ClO_2$ production. The $ClO_2$ production for both storage times were substantially equal during both time periods indicating that the storage for 27 days does not impact the ability of the sachet to react, as shown below in Table 7.

TABLE 7

Effect of Storage on Reactivity of Media

| Hours | Day 0 (Ave mg $ClO_2$) | Day 27 (Ave mg $ClO_2$) | % Production on Day 27 vs. Day 0 |
|---|---|---|---|
| 24 | 23.47 | 21.52 | 92% |
| 48 | 24.15 | 24.67 | 102% |

Effect of Varying Relative Humidity at 70° F. on Reactivity of Media

Sachets were suspended in containers at 70° F. at the indicated % RH and left for 3 hours. Sachets were moved to containers at 70° F. over 5% potassium iodide (KI) solution (99% RH) for 21 hours and the $ClO_2$ captured in the KI solution. KI Solution was titrated using Standard Methods Iodometric Titration technique to determine the $ClO_2$ concentration after 21 hours. The results indicate that the sachets were substantially equally reactive during the 21 hour time period indicating that the % RH does not impact the ability of the sachet to react, as shown in Table 8 below.

TABLE 8

Effect of Varying Relative Humidity
at 70° F. on Reactivity of Media

| % RH | Glatfelter Membrane (filter paper/membrane) (Ave mg $ClO_2$) | Glatfelter Membrane (filter paper/membrane) (Relative % Conversion) |
|---|---|---|
| 35 | 17.54 | 96.8% |
| 99 | 18.11 | 100.0% |

Effect of Varying Relative Humidity at 70° F. on Reactivity of Media

Sachets were suspended in containers at 70° F. at the indicated % RH and left for 3 hours. Sachets were moved to containers at 70° F. over 5% potassium iodide (KI) solution (99% RH) for 21 hours and the $ClO_2$ captured in the KI solution. The KI Solution was titrated using Standard Methods Iodometric Titration technique to determine the $ClO_2$ concentration after 21 hours. The results indicate that the sachets were substantially equally reactive during the 21 hour time period indicating that the % RH does not impact the ability of the sachet to react, as shown in Table 9 below.

TABLE 9

Effect of Varying Relative Humidity
at 70° F. on Reactivity of Media

| % RH | Glatfelter Membrane (filter paper/membrane) (Ave mg $ClO_2$) | Glatfelter Membrane (filter paper/membrane) (Relative % Conversion) |
|---|---|---|
| 50 | 16.85 | 93.1% |
| 99 | 18.11 | 100.0% |

Effect of Deliquescent on Reactivity of Media at Varying % RH

Sachets were suspended in containers at 70° F. at the indicated % RH and left for 3 hours. Sachets were moved to containers at 70° F. over 5% potassium iodide (KI) solution (99% RH) for 21 hours and the $ClO_2$ captured in the KI solution. KI Solution was titrated using the Standard Methods Iodometric Titration technique to determine the $ClO_2$ concentration after 21 hours. The results indicate that the sachets were significantly more reactive during the 21 hour time period when a deliquescent ($CaCl_2$) was added to the sachet, as shown in Table 10 below.

TABLE 10

Effect of Deliquescent on Reactivity of Media at Varying % RH
Reactivity with Deliquescent

| % RH | TYVEK ™ | TYVEK ™ & CaCl2 | % increase with CaCl2 |
|---|---|---|---|
| 35.00 | 6.91 | 14.00 | 202% |
| 50.00 | 5.11 | 15.01 | 294% |
| 99.00 | 8.08 | 18.08 | 224% |

Effect of Packaging Material on Reactivity of Media at 70° F. and Varying % RH

Sachets were suspended in containers at 70° F. at the indicated % RH and left for 3 hours. Sachets were moved to containers at 70° F. over 5% potassium iodide (KI) solution (99% RH) for 21 hours and the $ClO_2$ captured in the KI solution. KI Solution was titrated using the Standard Methods Iodometric Titration technique to determine the $ClO_2$ concentration after 21 hours. The results indicate that the sachets were significantly more reactive during the 21 hour time period when the Glatfelter paper was used versus porous polyethylene (TYVEK™) as the sachet membrane, as shown in Table 11 below.

TABLE 11

Effect of Packaging Material on Reactivity
of Media at 70° F. and Varying % RH
Reactivity Thru Differing Membrane Barriers

| % RH | TYVEK ™ (Average mg $ClO_2$) | Glatfelter Membrane (filter paper/membrane) (Average mg $ClO_2$) | % Increased Reactivity Glatfelter Membrane (filter paper/membrane) v. TYVEK ™ |
|---|---|---|---|
| 35 | 6.91 | 17.54 | 254% |
| 50 | 5.11 | 16.85 | 330% |
| 99 | 8.08 | 18.11 | 224% |

As shown in Table 12 below, additional testing with TYVEK at varied relative humidities (e.g., 35%, 50%, and 99%) was conducted to show that the sachet operates independent of humidity after 24 hours.

TABLE 12

TYVEK testing at varied relative humidities

| % RH | TYVEK ™ | % of control @ 99% RH |
|---|---|---|
| 35 | 6.91 | 86% |
| 50 | 5.11 | 63% |
| 99 | 8.08 | 100% |

As reflected in the examples above, a proton-generating species can be mixed in the same enclosure with an impregnate comprising a chlorine dioxide precursor impregnated in a porous carrier to form a mixture capable of producing chlorine dioxide gas when exposed to a source of humidity. Further, the examples provide exemplary data regarding various factors that can be modified to adjust properties of the mixture and/or the rate at which chlorine dioxide is produced.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A mixture for producing chlorine dioxide gas provided in an enclosure, comprising:
   an impregnate comprising a chlorine dioxide precursor impregnated in a porous carrier; and
   a proton-generating species;
   wherein the impregnate and the proton-generating species are intermixed to produce a mixture and the mixture is provided in an enclosure;
   wherein the amount of chlorine dioxide produced in 24 hours when the enclosure is opened after 27 days of storage is 90% or greater of the amount of chlorine dioxide produced in 24 hours when the enclosure is opened after 0 days of storage; and
   wherein the enclosure is a humidity-activated sachet and the mixture is enclosed within a membrane.

2. A mixture for producing chlorine dioxide gas provided in an enclosure, comprising:
   an impregnate comprising a chlorine dioxide precursor impregnated in a porous carrier; and
   a proton-generating species;
   wherein the impregnate and the proton-generating species are intermixed to produce a mixture and the mixture is provided in an enclosure;
   wherein the amount of chlorine dioxide produced in 24 hours when the enclosure is opened and exposed to a temperature of 70° F. and a relative humidity of 50% is 90% or greater of the amount of chlorine dioxide produced in 24 hours when the enclosure is opened and exposed to a temperature of 70° F. and a relative humidity of 99%, and
   wherein the enclosure is a humidity-activated sachet and the mixture is enclosed within a membrane.

3. The mixture according to claim 2, wherein the porous carrier is zeolite, diatomaceous earth, silica, alumina, porous polymer, clay, or a mixture thereof.

4. The mixture according to claim 2, wherein said impregnate is treated with a base.

5. The mixture according to claim 4, wherein said base is potassium hydroxide, sodium hydroxide, calcium hydroxide, or a blend thereof.

6. The mixture according to claim 2, further comprising a water-retaining substance selected from the group consisting of calcium chloride, magnesium sulfate, potassium chloride, and mixtures thereof.

7. The mixture according to claim 6, wherein the water-retaining substance is impregnated in a porous carrier.

8. The mixture according to claim 2, wherein the chlorine dioxide precursor is selected from the group consisting of metal chlorites, metal chlorates, chloric acid, hypochlorous acid, and mixtures thereof.

9. The mixture according to claim 2, wherein the proton-generating species is an inorganic acid, an organic acid, or a salt or mixture thereof.

10. The mixture according to claim 2, wherein the proton-generating species comprises a metal salt selected from the group consisting of sodium bisulfate, disodium hydrogen phosphate, ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, sodium citrate, and mixtures thereof.

11. The mixture according to claim 2, wherein the proton-generating species is in the form of a powder or crystals.

12. The mixture according to claim 2, wherein the proton-generating species is impregnated in a porous carrier, and wherein porous carrier is zeolite, diatomaceous earth, silica, alumina, porous polymer, clay, or a mixture thereof.

13. The mixture according to claim 2, wherein the proton-generating species is provided in excess of the stoichiometric amount.

14. The mixture according to claim 2, wherein the impregnate comprises sodium chlorite.

15. A mixture for producing chlorine dioxide gas provided in an enclosure, comprising:
   an impregnate comprising a chlorine dioxide precursor impregnated in a porous carrier; and
   a proton-generating species;
   wherein the impregnate and the proton-generating species are intermixed to produce a mixture and the mixture is provided in an enclosure;
   wherein the amount of chlorine dioxide produced in 24 hours when the enclosure is opened and exposed to a temperature of 70° F. and a relative humidity of 35% is 85% or greater of the amount of chlorine dioxide produced in 24 hours when the enclosure is opened and exposed to a temperature of 70° F. and a relative humidity of 99%; and wherein the enclosure is a humidity-activated sachet and the mixture is enclosed within a membrane.

16. The mixture according to claim 15, wherein the amount of chlorine dioxide produced in 24 hours when the enclosure is opened and exposed to a temperature of 70° F. and a relative humidity of 35% is 90% or greater of the amount of chlorine dioxide produced in 24 hours when the enclosure is opened and exposed to a temperature of 70° F. and a relative humidity of 99%.

17. A method of limiting the production of bio-organisms in a food package, comprising providing the mixture in an enclosure according to claim 2, and wherein the food package includes a fruit, a vegetable, or a mixture thereof.

18. The mixture according to claim 1, wherein the impregnate is dried to 5% water or less.

19. The mixture according to claim 1, wherein the enclosure does not include a water-retaining substance.

20. The mixture according to claim 2, wherein the impregnate is dried to 5% water or less.

21. The mixture according to claim 2, wherein the enclosure does not include a water-retaining substance.

22. The mixture according to claim 15, wherein the impregnate is dried to 5% water or less.

23. The mixture according to claim 15, wherein the enclosure does not include a water-retaining substance.

24. A method of limiting the production of bio-organisms in a food package, comprising providing the mixture in an enclosure according to claim 1, and wherein the food package includes a fruit, a vegetable, or a mixture thereof.

25. A method of limiting the production of bio-organisms in a food package, comprising providing the mixture in an enclosure according to claim 15, and wherein the food package includes a fruit, a vegetable, or a mixture thereof.

* * * * *